(12) United States Patent
Tang et al.

(10) Patent No.: US 10,421,715 B2
(45) Date of Patent: Sep. 24, 2019

(54) PLEUROMUTILIN DERIVATIVE HAVING 2-AMINO PHENYL MERCAPTAN SIDE CHAIN AS WELL AS PREPARATION METHOD AND APPLICATION THEREOF

(71) Applicant: SOUTH CHINA AGRICULTURAL UNIVERSITY, Guangzhou (CN)

(72) Inventors: Youzhi Tang, Guangzhou (CN); Yahong Liu, Guangzhou (CN); Zhaosheng Zhang, Guangzhou (CN)

(73) Assignee: SOUTH CHINA AGRICULTURAL UNIVERSITY, Ghangzhou (CN)

( * ) Notice: Subject to any disclaimer, the term of this patent is extended or adjusted under 35 U.S.C. 154(b) by 0 days.

(21) Appl. No.: 16/236,370

(22) Filed: Dec. 29, 2018

(65) Prior Publication Data

US 2019/0135742 A1    May 9, 2019

Related U.S. Application Data

(63) Continuation of application No. PCT/CN2016/101097, filed on Sep. 30, 2016.

(51) Int. Cl.
| | | |
|---|---|---|
| *C07C 303/28* | (2006.01) | |
| *C07C 323/63* | (2006.01) | |
| *C07C 319/20* | (2006.01) | |
| *C07C 319/14* | (2006.01) | |
| *C07C 309/73* | (2006.01) | |
| *C07C 323/52* | (2006.01) | |
| *A61P 31/04* | (2006.01) | |

(52) U.S. Cl.
CPC ............ *C07C 323/63* (2013.01); *A61P 31/04* (2018.01); *C07C 303/28* (2013.01); *C07C 309/73* (2013.01); *C07C 319/14* (2013.01); *C07C 319/20* (2013.01); *C07C 323/52* (2013.01); *C07C 2603/82* (2017.05)

(58) Field of Classification Search
None
See application file for complete search history.

(56) References Cited

U.S. PATENT DOCUMENTS

| 6,121,281 A | 9/2000 | Takle et al. |
| 6,784,193 B1 | 8/2004 | Ascher et al. |
| 7,534,814 B2 | 5/2009 | Ascher et al. |
| 2010/0197909 A1 | 8/2010 | Fukuda et al. |

OTHER PUBLICATIONS

Internation Search Report of PCT/CN2016/101097, dated Jul. 7, 2017.

*Primary Examiner* — Ana Z Muresan
(74) *Attorney, Agent, or Firm* — W&K IP

(57) ABSTRACT

A pleuromutilin derivative having a 2-amino phenyl mercaptan side chain as well as a preparation method and application thereof are provided. The derivative has a structure represented by formula 2 or formula 3, wherein, R1, R2 and R3 are each independently selected from a hydrogen atom, hydroxyl, amino, sulfydryl, hydroxymethyl, amine methyl, nitro, halogen, trihalogenated methyl, methyl, natural amino acid acylamino and C1-6 alkoxy. The plueuromutilin derivative in the disclosure has good activity of inhibiting drug-resistant *Staphylococcus aureus* and *mycoplasma*, and is especially suitable for preventing and treating infectious diseases caused by human or animal *mycoplasma* or drug-resistant *Staphylococcus aureus* or multidrug resistant bacteria as a novel antibacterial drug.

4 Claims, No Drawings

PLEUROMUTILIN DERIVATIVE HAVING 2-AMINO PHENYL MERCAPTAN SIDE CHAIN AS WELL AS PREPARATION METHOD AND APPLICATION THEREOF

CROSS-REFERENCE TO RELATED APPLICATIONS

This application is a continuation of International Patent Application No. PCT/CN2016/101097 with a filing date of Sep. 30, 2016, designating the United States, now pending. The content of the aforementioned applications, including any intervening amendments thereto, are incorporated herein by reference.

TECHNICAL FIELD

The disclosure belongs to the field of pharmaceutical chemistry, and particularly relates to a pleuromutilin derivative having a 2-amino phenyl mercaptan side chain as well as a preparation method and an application thereof.

BACKGROUND OF THE PRESENT INVENTION

Methicillin-resistant *Staphylococcus aureus* (MRSA) is a pathogenic bacterium which is wide in prevalent range, strong in pathogenicity and high in morbidity and mortality. Once a human body is infected, symptoms such as fever, poor spirit and local infection are caused, the most common symptom is pulmonary infection, other symptoms include skin, urinary tract and pregnant woman's reproductive tract infections, the serious symptom is septicemia, so that length of stay of a patient is delayed, and life of the patient can be endangered without timely treatment. An investigation from Dutch in 2003 reveals that about 39% of slaughtered pigs contain ST398 type MRSA, and 27% of feeders carry pig-derived MRSA. Animal-derived MRSA ST398 can cause infection of humans contacting with animals. MRSA can resist all of 13 amide antibiotics and resist most of macrolide, aminoglycoside and fluoroquinolone antibacterial drugs and the like, leading to a fact that infection caused by this bacterium is difficult to treat and high in fatality rate.

Pleuromutilin (formula I) is produced by higher fungi *Pleurotusmutilize (Fr.) Sacc.* and *Pleurotus Passecheranius Pilat*, and is a tricylic diterpene compound having a combined (5-6-8)tricycle. The compounds and a ribosome 50S subunit interact to inhibit synthesis of bacterial proteins. The compounds have strong antibacterial activity on drug-resistant gram-positive bacteria, drug-resistant *mycoplasma* and partial gram-negative bacteria. The pleuromutilin compounds have a nuclear parent structure different from those of clinically common antibacterial drugs, and difficultly generate cross drug resistance with antibacterial drugs having other structures. Through modification of a pleuromutilin C14 side chain, two pleuromutilin veterinary antibacterial drugs Tiamulin and Valnemulin have entered a market at present.

As a first human pleuromutilin antibacterial drug, retapamulin was approved by Food and Drug Administration (FDA) of America to be marketed in 2007. It is mainly used for treatment of pustule atopic dermatitis caused by *Staphylococcus aureus* and *Streptococcus pyogenes* infections. Retapamulin has good antibacterial activity on multiple drug-resistant bacteria such as clinically common antibacterial drugs including oxacillin, erythrocin and mupirocin. It is also found that retapamulin more difficultly causes drug resistance of *Staphylococcus aureus* compared with traditional antibacterial drugs.

Since the mechanism of the pleuromutilin compound is different from that of antibiotics widely applied in clinic, there are few drug-resistance bacteria for pleuromutilin antibacterial drugs. Compared with dozens of drugs successfully developed based on the same nuclear parent with penicillin, cephalosphorin and floxacin antibacterial drugs, there are only three antibacterial drugs to be successfully developed based on pleuromutilin. The disclosure will provide a novel pleuromutilin compound having novel structures and strong antibacterial activity.

Formula I

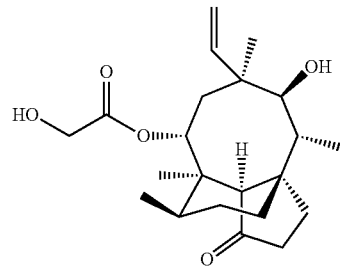

SUMMARY OF PRESENT INVENTION

In order to solve the above defects existing in the prior art, a main objective of the disclosure is to provide a pleuromutilin derivative having a 2-amino phenyl mercaptan side chain.

Another objective of the disclosure is to provide a preparation method of the pleuromutilin derivative having a 2-amino phenyl mercaptan side chain.

Still another objective of the disclosure is to provide a pharmaceutical composition, comprising the pleuromutilin derivative having a 2-amino phenyl mercaptan side chain as an active component.

Still yet another objective of the disclosure is to provide application of the above pleuromutilin derivative having a 2-amino phenyl mercaptan side chain in preparation of a drug for treating infectious diseases, especially infectious diseases caused by *mycoplasma* or drug-resistant *Staphylococcus aureus* or multidrug resistant bacteria infections.

The objectives of the disclosure are achieved by the following technical solutions.

A pleuromutilin derivative having a 2-amino phenyl mercaptan side chain is provided, and the pleuromutilin derivative is a compound having a structure represented by formula 2 or a pharmaceutically acceptable salt thereof, or a compound having a structure represented by formula 3 or a pharmaceutically acceptable salt thereof:

Formula 2

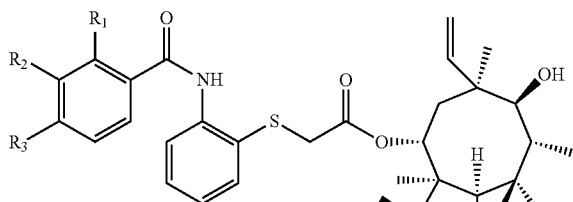

Formula 3

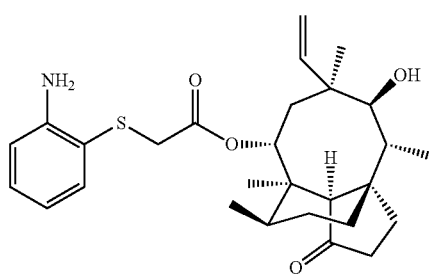

wherein, $R_1$ is one of a hydrogen atom, hydroxyl, amino, sulfydryl, hydroxymethyl, amine methyl, nitro, halogen, trihalogenated methyl, methyl, natural amino acid acylamino and C1-6 alkoxy;

$R_2$ is one of a hydrogen atom, hydroxyl, amino, sulfydryl, hydroxymethyl, amine methyl, nitro, halogen, trihalogenated methyl, methyl, natural amino acid acylamino and C1-6 alkoxy; and $R_3$ is one of a hydrogen atom, hydroxyl, amino, sulfydryl, hydroxymethyl, amine methyl, nitro, halogen, trihalogenated methyl, methyl, natural amino acid acylamino and C1-6 alkoxy.

Preferably, $R_1$ is one of hydrogen atom, hydroxyl, amino, hydroxymethyl, amine methyl, fluorine, trifluoromethyl, nitro, trifluoromethyl, methoxy, ethoxyl, prolyl amino and valyl amino; $R_2$ is one of hydrogen atom, hydroxyl, amino, hydroxymethyl, amine methyl, fluorine, trifluoromethyl, nitro, trifluoromethyl, methoxy, ethoxyl, prolyl amino and valyl amino; and $R_3$ is one of hydrogen atom, hydroxyl, amino, hydroxymethyl, amine methyl, fluorine, trifuoromethyl, nitro, trifluoromethyl, methoxy, ethoxyl, prolyl amino and valyl amino.

The term "halogen" represents fluorine, chlorine, bromine and iodine.

More preferably, $R_1$ is methyl, $R_2$ is a hydrogen atom, and $R_3$ is a hydrogen atom; or $R_1$ is a hydrogen atom, $R_2$ is methyl, and $R_3$ is a hydrogen atom; or $R_1$ is a hydrogen atom, $R_2$ is a hydrogen atom, and $R_3$ is methyl; or $R_1$ is a fluorine atom, $R_2$ is a hydrogen atom, and $R_3$ is a hydrogen atom; or $R_1$ is a hydrogen atom, $R_2$ is a fluorine atom, and $R_3$ is a hydrogen atom; or $R_1$ is a hydrogen atom, $R_2$ is a hydrogen atom, and $R_3$ is a fluorine atom; or $R_1$ is a chlorine atom, $R_2$ is a hydrogen atom, and $R_3$ is a hydrogen atom; or $R_1$ is a hydrogen atom, $R_2$ is a chlorine atom, and $R_3$ is a hydrogen atom; or $R_1$ is a hydrogen atom, $R_2$ is a hydrogen atom, and $R_3$ is a chlorine atom; or $R_1$ is methoxy, $R_2$ is a hydrogen atom, and $R_3$ is a hydrogen atom; or $R_1$ is a hydrogen atom, $R_2$ is methoxy, and $R_3$ is a hydrogen atom; or $R_1$ is a hydrogen atom, $R_2$ is a hydrogen atom, and $R_3$ is methoxy.

The above preferred embodiments are also shown in Table 1

TABLE 1

Structural formulas of representative compounds 1-12 of the disclosure

| Compound | $R_1$ = | $R_2$ = | $R_3$ = |
|---|---|---|---|
| 1 | —CH$_3$ | —H | —H |
| 2 | —H | —CH$_3$ | —H |
| 3 | —H | —H | —CH$_3$ |
| 4 | —F | —H | —H |
| 5 | —H | —F | —H |
| 6 | —H | —H | —F |
| 7 | —Cl | —H | —H |
| 8 | —H | —Cl | —H |
| 9 | —H | —H | —Cl |
| 10 | —OCH$_3$ | —H | —H |
| 11 | —H | —OCH$_3$ | —H |
| 12 | —H | —H | —OCH$_3$ |

The pharmaceutically acceptable salt is formed by the compound having the structure represented by formula 2 or formula 3 and an acid of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

Preferably, structural formulas of partial representative pharmaceutically acceptable salts formed by the compounds represented by formula 2 and formula 3 are shown in Table 2.

TABLE 2

Partial representative pharmaceutically acceptable salts

| Compound | Structrual formula |
|---|---|
| 14 | 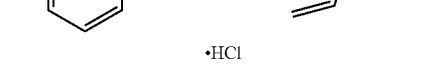 •HCl |
| 15 |  •H$_2$SO$_4$ |

TABLE 2-continued

Partial representative pharmaceutically acceptable salts

| Compound | Structrual formula |
|---|---|
| 16 | 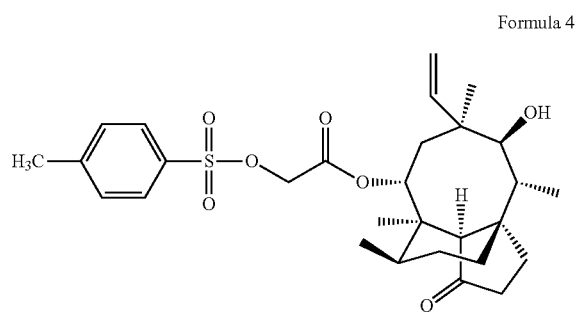 |

A method for preparing the above pleuromutilin derivative having a 2-amino phenyl mercaptan side chain, comprises the following steps:

(1) reacting pleuromutilin with paratoluensulfonyl chloride to obtain an intermediate I having a structure represented by formula 4;

Formula 4

(2) reacting the intermediate I serving as a raw material with sodium iodide to be further activated, and then reacting a resulting product with 2-amino phenyl mercaptan under an alkaline condition to obtain an intermediate II having the structure represented by formula 3; and (3) reacting the intermediate II serving as a raw material with various substituted benzoic acids to obtain the pleuromutilin derivative having the structure represented by formula 2.

The reaction in step (1) is carried out for 3 hours at 0° C. with pyridine as a solvent; a molar ratio of paratoluensulfonyl chloride to pleuromutilin is 1.1:1.

The reaction in step (2) is that a non-protonic solvent is used as a solvent, the intermediate I is dissolved into the non-protonic solvent at first, wherein, an amount of the solvent is 30 times the mass of the intermediate I; then anhydrous sodium iodide is added, and heating reflux is carried out for 1 hour, wherein, a molar ratio of the intermediate I to anhydrous sodium iodide is 1:1.1; prior to the reaction, 2-amino phenyl mercaptan and alkali are dissolved into water, and then subjected to heating reflux for 2 hours together with a product obtained by activation, wherein, a molar ratio of the intermediate I to 2-amino phenyl mercaptan is 1:1.1, and a molar ratio of 2-amino phenyl mercaptan to alkali is 1:2; the alkali is sodium hydroxide, potassium hydroxide, cesium hydroxide, sodium carbonate, potassium carbonate or cesium carbonate; the non-protonic solvent is N,N-dimethylformamide.

The reaction in step (3) is that a non-protonic solvent is used as a solvent, substituted benzoic acid is added and then condensed for 1-36 hours with the intermediate II at 0-70° C. in the presence of a condensing agent and alkali, heating and stirring are carried out to obtain a target product, and recrystallization or column chromatographic purification is carried out; wherein, the non-protonic solvent is dichloromethane, ethyl acetate, N,N-dimethylformamide, N,N-dimethydimethylacetamide or pyridine; the condensing agent is methyl chloroformate, ethyl chloroformate, terbutyl chloroformate, carbonyl diimidazole (CDI), sulfonyl chloride, Boc anhydride, N,N-dicyclohexyl carbodiimide (DCC), 6-chlorobenzotriazole-1,1,3,3-tetramethylurea hexafluorophosphate (HCTU), O-benzotriazole-N,N,N'N'-tetramethylurea tetrafluoroboric acid (TBTU), 2-(7-oxidized benzotriazole)-N,N,N'N'-tetramethylurea hexafluorophosphate (HATU), 1-(3-dimethylaminopropyl)-3-ethyl carbodiimide (EDC), 1-hydroxyl-benzotriazole (HOBt) or 1H-benzotriazole-1-oxytripyrrolidyl hexafluorophosphate (PyBOP), oxalyl chloride or thionyl chloride; the alkali is pyridine, triethylamine, morpholine, N-methylmorpholine or N,N-diisopropylethyl amine (DIEA).

A synthetic routine is as follows:

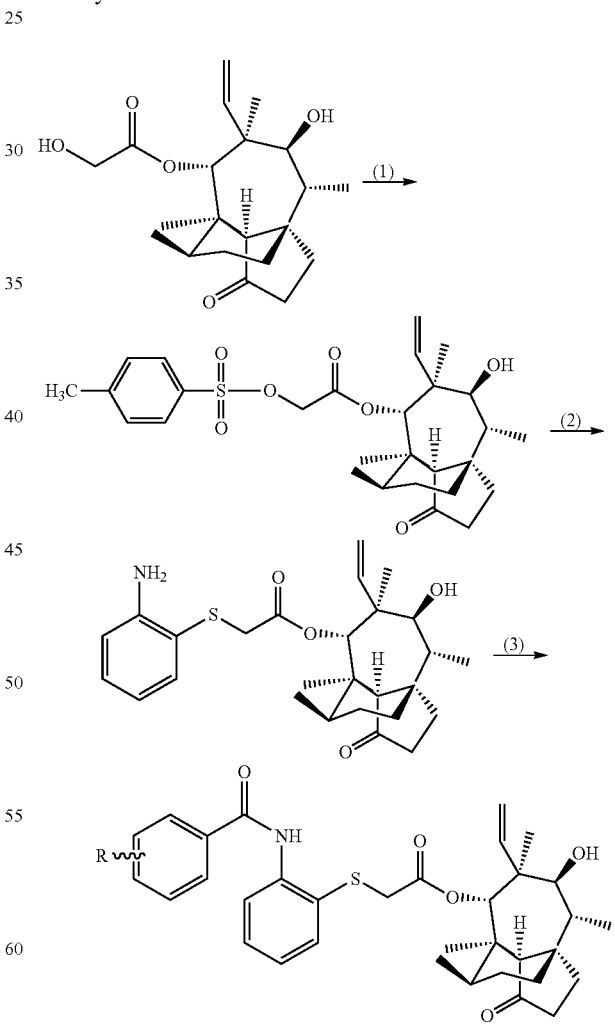

A pharmaceutical composition, comprises the above pleuromutilin derivative having a 2-amino phenyl mercaptan side chain as an active component.

An application of the pleuromutilin derivative having a 2-amino phenyl mercaptan side chain in preparation of a drug for treating infectious diseases, wherein, the infectious diseases are infectious diseases caused by a fact that humans or animals are infected by *mycoplasma* or drug resistant *Staphylococcus aureus* or multidrug resistant bacteria.

Compared with the existing technologies, the disclosure has the following advantages and beneficial effects that the pleuromutilin derivative provided by the disclosure is a novel compound reported for the first time. Through wide and deep research, the inventors synthesize a large amount of compounds and perform wide bioactivity screen, so that it is firstly found that compounds of formula 2 and formula 3 have good in-vitro antibacterial activity, and are especially suitable for whole body system infection of animals or humans as a novel antibacterial drug.

DETAILED DESCRIPTION OF PREFERRED EMBODIMENTS

The disclosure will be further described in combination with examples, but embodiments of the disclosure are not limited thereto. Numbers of compounds obtained in the following examples 1-12 are as shown in claims.

An Example of Preparation of an Intermediate I 5.4 g (14.27 mmol) of pleuromutilin was dissolved into 30 ml of pyridine and subjected to ice bath until a temperature reaches about 0° C., and 8.6 g (45.11 mmol) of paratoluensulfonyl chloride was added. After the reaction was carried out for 3 h on ice bath under the condition of stirring, 50 ml of ice water was added for quenching reaction. A reaction liquid was poured into a separating funnel, 50 ml of chloroform was added at first for layering, a water phase was removed, subsequently, 100 ml of 2 mol/L sulfuric acid solution was used to wash an organic phase twice, then 50 ml of saturated sodium bicarbonate solution was used to wash the organic phase twice, and finally, 100 ml of deionized water was used to wash the organic phase twice and then the organic phase was dried using anhydrous sodium sulfate. Rotary evaporation was carried out on the organic phase, the residual solid was added with 10 ml of isopropanol and dissolved by heating, a large amount of white powders were separated out after cooling, suction filtration was carried out, a filtrate was washed with isopropanol, and the residual liquid of the product while powder was naturally volatilized to be dried. The obtained white powder was the intermediate I. The yield was 88.84%.

An Example of Preparation of an Intermediate II (a Compound of Formula 3, a Compound 13)

1 g (1.88 mmol) of intermediate I was dissolved into 35 ml of ethyl acetate, 0.31 g (2.07 mmol) of anhydrous sodium iodide was added, and heating and stirring were carried out at about 70° C. to react for 1 h. 0.25 g (2.04 mmol) of 2-amino phenyl mercaptan was taken and placed into 10 ml of water, 0.08 g (2.04 mmol) of sodium hydroxide was added into aqueous solution, the above aqueous solution was added into a reaction system, and heating and stirring were carried out at about 70° C. to react for 2 h. A reaction liquid was poured into a separating funnel, 30 ml of chloroform was added for extraction, and an organic phase was taken. Rotary evaporation was carried out on the obtained organic phase to obtain a mixture, the obtained mixture was redissolved with dichloromethane, 1 g of silica gel having 100-200 meshes was added and sufficiently mixed, the above crude product-silica gel powder mixture is purified via column chromatography (silica gel powder having 200-300 meshes was a stationary phase, and a mobile phase was composed of petroleum ether and ethyl acetate in a ratio of 1:2) after the solvent is completely volatilized, so as to obtain a purified product of the intermediate II having a structure of formula 3. The yield was 81.22%.

Example 1: synthesis of
22-O-[2-(2-methylbenzamido) phenyl] thioacetyl valnemulin (compound 1)

0.82 g (1.88 mmol) of intermediate II was dissolved into 35 ml of ethyl acetate, 2-methyl benzoic acid (2.07 mmol) and 2.07 mmol of oxalyl chloride were added, and heating and stirring were carried out at about 70° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(2-methylbenzamide) phenyl] thioacetyl valnemulin (compound 1). The yield was 86.55%. HR-MS (ESI): Cal: 604.3091; Found: 604.3117.

Example 2: synthesis of
22-O-[2-(3-methylbenzamnido) phenyl] thioacetyl valnemulin (compound 2)

0.82 g (1.88 mmol) of intermediate II was dissolved into 35 ml of dichloromethane, 3-methyl benzoic acid (2.07 mmol) and 2.07 mmol of ter-butyl chloroformate were added, and heating and stirring were carried out at about 70° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(3-methylbenzamide) phenyl] thioacetyl valnemulin (compound 2). The yield was 85.75%. HR-MS (ESI): Cal: 604.3091; Found: 604.3110.

Example 3: synthesis of
22-O-[2-(4-methylbenzamido) phenyl] thioacetyl valnemulin (compound 3)

0.82 g (1.88 mmol) of intermediate II was dissolved into 35 ml of dichloromethane, 4-methyl benzoic acid (2.07 mmol) and 2.07 mmol of thionyl chloride were added, and heating and stirring were carried out at about 70° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(4-methylbenzamido) phenyl] thioacetyl valnemulin (compound 3). The yield was 83.09%. HR-MS (ESI): Cal: 604.3091; Found: 604.3110.

Example 4: synthesis of 22-O-[2-(2-fluorobenzamido) phenyl] thioacetyl valnemulin (compound 4)

0.82 g (1.88 mmol) of intermediate II was dissolved into 35 ml of N,N-dimethylformamide, 2.06 mmol of 2-fluorobenzoic acid, 2.06 mmol of 1H-benzotriazole-1-oxytripyrrolidyl hexafluorophosphate and 6 mmol of N,N-diisopropylethylamine were added, and heating and stirring were carried out at about 70° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(2-fluorobenzamido) phenyl] thioacetyl valnemulin (compound 4). The yield was 91.47%. HR-MS (ESI): Cal: 608.2840; Found: 608.2867.

Example 5: synthesis of 22-O-[2-(3-fluorobenzamido) phenyl] thioacetyl valnemulin (compound 5)

0.82 g (1.88 mmol) of intermediate II was dissolved into 35 ml of ethyl acetate, 3-fluorobenzoic acid (2.06 mmol), 2.06 mmol of 6-chlorobenznotriazole-1,1,3,3-tetramethylurea hexafluorophosphate and 6 mmol of triethylamine were added, and heating and stirring were carried out at about 70° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(3-fluorobenzamido) phenyl] thioacetyl valnemulin (compound 5). The yield was 87.39%. HR-MS (ESI): Cal: 608.2840; Found: 608.2856.

Example 6: synthesis of 22-O-[2-(4-fluorobenzamido) phenyl] thioacetyl valnemulin (compound 6)

0.82 g (1.88 mmol) of intermediate II was dissolved into 35 ml of dichloromethane, 4-fluorobenzoic acid (2.06 mmol) and 2.06 mmol of carbonyldiimidazole were added, and stirring was carried out at room temperature to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(4-fluorobenzamido) phenyl] thioacetyl valnemulin (compound 6). The yield was 84.91%. HR-MS (ESI): Cal: 608.2840; Found: 608.2836.

Example 7: synthesis of 22-O-[2-(2-chlorobenzamido) phenyl] thioacetyl valnemulin (compound 7)

0.82 g (1.88 mmol) of intermediate II was dissolved into 35 ml of ethyl acetate, 2-chlorobenzoic acid (2.06 mmol) and 2.06 mmol of 1-(3-dimethyl amino propyl)-3-ethyl carbondiimine were added, and heating and stirring were carried out at 50° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(2-chlorobenzamido) phenyl] thioacetyl valnemulin (compound 7). The yield was 87.86%. HR-MS (ESI): Cal: 624.2545; Found: 624.2575.

Example 8: synthesis of 22-O-[2-(3-chlorobenzamido) phenyl] thioacetyl valnemulin (compound 8)

0.82 g (1.88 mmol) of intermediate II was dissolved into 35 ml of N,N-dimethylformamide, 2.06 mmol of 3-chlorobenzoic acid and 2.06 mmol of N,N-bicyclohexylcarbondiimine were added, and heating and stirring were carried out at 25° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(3-chlorobenzamido) phenyl] thioacetyl valnemulin (compound 8). The yield was 85.04%. HR-MS (ESI): Cal: 624.2545; Found: 624.2562.

Example 9: synthesis of 22-O-[2-(4-chlorobenzamido) phenyl] thioacetyl valnemulin (compound 9)

0.82 g (1.88 mmol) of intermediate II was dissolved into 35 ml of N,N-dimethylacetamide, 2.06 mmol of 4-chlorobenzoic acid and 2.06 mmol of carbonyldiimidazole were added, and heating and stirring were carried out at about 30° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(4-chlorobenzamido) phenyl] thioacetyl valnemulin (compound 9). The yield was 89.66%. HR-MS (ESI): Cal: 624.2545; Found: 624.2540.

Example 10: synthesis of 22-O-[2-(2-methoxybenzamido) phenyl] thioacetyl valnemulin (compound 10)

0.82 g (1.88 mmol) of intermediate II was dissolved into 35 ml of ethyl acetate, 2.05 mmol of 2-methoxybenzoic acid, 2.05 mmol of methyl chloroformate and 2.5 mmol of morpholine were added, and stirring were carried out at 25° C. to react for 1 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(2-methoxybenzamido) phenyl] thioacetyl valnemulin (compound 10). The yield was 92.24%. HR-MS (ESI): Cal: 620.3040; Found: 620.3037.

Example 11: synthesis of 22-O-[2-(3-methoxybenzamido) phenyl] thioacetyl valnemulin (compound 11)

0.82 g (1.88 mmol) of intermediate II was dissolved into 35 ml of N,N-dimethylacetamide, 2.05 mmol of 3-methoxybenzoic acid and 2.05 mmol of O-benzotriazole-N,N,N',N'-tetramethylurea tetraboric acid and 6 mmol of N-methyl morpholine were added, and stirring were carried out at 0° C. to react for 3 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after the solvent was completely volatilized, so as to obtain a purified product of 22-O-[2-(3-methoxybenzamido) phenyl] thioacetyl valnemulin (compound 11). The yield was 94.82%. HR-MS (ESI): Cal: 620.3040; Found: 620.3062.

Example 12: synthesis of 22-O-[2-(4-methoxybenzamido) phenyl] thioacetyl valnemulin (compound 12)

0.82 g (1.88 mmol) of intermediate II was dissolved into 35 ml of ethyl acetate, 2.05 mmol of 4-methoxybenzoic acid and 2.05 mmol of ethyl chloroformate were added, and heating and stirring were carried out at 70° C. to react for 36 h to obtain a target product. Rotary evaporation was carried out on the obtained mixed solution to obtain a mixture, the obtained mixture was redissolved with dichloromethane, 1 g of silica gel having 100-200 meshes was added and sufficiently mixed, and the above crude product-silica gel powder mixture was purified via column chromatography (silica gel powder having 200-300 meshes was a stationary phase, and a mobile phase was composed of petroleum ether and ethyl acetate in a ratio of 1:1) after a solvent was completely volatilized, so as to obtain a purified product of 22-O-[2-(4-methoxybenzamido) phenyl] thioacetyl valnemulin (compound 11). The yield was 87.07%. HR-MS (ESI): Cal: 620.3040; Found: 620.3067.

Experiment Example: In-Vitro Bacteriostatic Experiment

Experimental Method

Minimum inhibitory concentrations (MIC) of a series of compounds obtained in the disclosure were measured by using a two-fold agar dilution method. An experimental control drug selected valnemulin, and valnemulin belongs to pleuromutilin antibiotics and is the most widely applied veterinary antibiotic in the pleuromutilin antibiotics at present. By using a multi-point inoculator, bacteria solution was inoculated into a culture dish containing drugs having different concentrations at a bacteria inoculating amount of $10^6$ CFU/ml. A result was observed after incubation for 24 hours at 37° C., and the concentration of a compound in a culture dish without bacteria served as the minimum inhibitory concentration (MIC) of this compound.

Strains used in the experiment were *E. Coli* ATCC25922, *Staphylococcus aureus* ATCC29213, methicillin-resistant *staphylococcus* ATCC43300 and *mycoplasma* gallisepticum S6.

25.6 mg of synthesized target compound was precisely weighed to be placed in 10 mL of volumetric flask and dissolved with a small amount of N,N-dimethylformamide and then a volume was metered with N,N-dimethylformamide to 10 mL, so as to prepare 2560 μg/mL stock solution. In addition, 25.6 mg of pleuromutilin, tiamulin, valnemulin and retapamulin were respectively and precisely weighed to be placed in 10 ml of volumetric flask, and a volume was metered with N,N-dimethylformamide to 10 mL, so as to prepare 2560 μg/mL control stock solution.

The control stock solution was diluted in a culture dish with a doubling dilution method, each culture dish contained 1 ml of medicine liquid, the medicine liquid is diluted to 20 ml with molten MH agar, so that final concentrations of subject compounds in a series of culture dishes were respectively 64, 32, 16, 8, 4, 2, 1, 0.5, 0.25, 0.125 and 0.0625 μg/ml.

MIC results are shown in Table 3 below.

TABLE 3 in-vitro bacteriostasis data

| Compound/material | *E. coli* ATCC25922 | *S. aureus* ATCC29213 | MRSA ATCC43300 | S6 |
|---|---|---|---|---|
| 1 | >64 | 0.25 | 0.25 | 0.125 |
| 2 | >64 | 1 | 0.5 | 0.25 |
| 3 | >64 | 0.5 | 0.5 | 0.25 |
| 4 | >64 | 0.5 | 0.5 | 0.25 |
| 5 | >64 | 0.125 | 0.125 | 0.125 |
| 6 | >64 | 1 | 1 | 0.5 |
| 7 | >64 | 0.5 | 0.5 | 0.25 |
| 8 | >64 | 0.25 | 0.25 | 0.125 |
| 9 | >64 | 0.5 | 0.5 | 0.25 |
| 10 | >64 | 1 | 0.5 | 0.25 |
| 11 | >64 | 1 | 1 | 0.25 |
| 12 | >64 | 1 | 1 | 0.5 |
| 13 | >64 | 0.0156 | 0.0156 | 0.0156 |
| Pleuromutilin, | >64 | 1 | 0.5 | 0.0625 |
| Tiamulin | >64 | 0.5 | 0.5 | 0.0156 |
| Valnemulin | 32 | 0.0625 | 0.0625 | 0.0039 |
| Retapamulin | — | 0.0625 | 0.0625 | — |

All of target compounds exhibit good antibacterial activity on *staphylococcus*, the antibacterial activity of most compounds on *staphylococcus* and methicillin-resistant *staphylococcus* is close to or superior to that of tiamulin widely used in clinic, the bacterial activity of a compound 13 on *staphylococcus* and methicillin-resistant *staphylococcus* is obviously superior to that of valnemulin and retapamulin widely used in clinic.

The above examples are preferred embodiments of the disclosure, but embodiments of the disclosure are not limited by the above examples, and changes, modifications, substitutions, combinations and simplifications made without departing from the spirit and principle of the disclosure are all equivalent replacement modes and are included within the protective scope of the disclosure.

We claim:

1. A method for preparing a pleuromutilin derivative having a 2-amino phenyl mercaptan side chain, comprising the following steps:

(1) reacting pleuromutilin with paratoluensulfonyl chloride to obtain an intermediate I having a structure of formula 4;

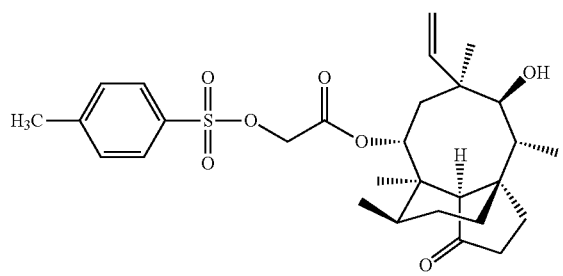

Formula 4

(2) reacting the intermediate I with sodium iodide to be further activated, and then reacting a resulting product with 2-amino phenyl mercaptan under an alkaline condition to obtain an intermediate II having the structure of formula 3; and

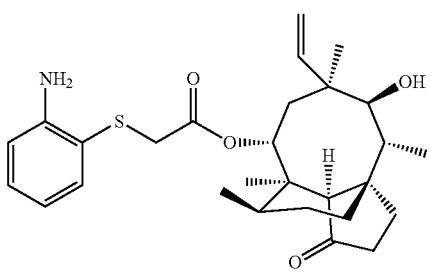

Formula 3

(3) reacting the intermediate II with various substituted benzoic acids in the presence of a condensing agent to obtain the pleuromutilin derivative having the structure of formula 2;

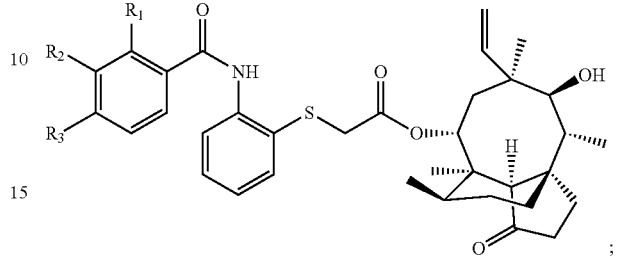

Formula 2 wherein, $R_1$ $R_2$ and $R_3$ are each independently selected from the group consisting of hydrogen atom, hydroxyl, amino, sulfydryl, hydroxymethyl, amine methyl, nitro, halogen, trihalogenated methyl, methyl, and C1-6 alkoxy.

2. The method according to claim 1, wherein, the reaction in step (1) is carried out for 3 hours at 0° C. with pyridine as a solvent; a molar ratio of paratoluensulfonyl chloride to pleuromutilin is 1.1:1.

3. The method according to claim 1, wherein, the reaction in step (2) is carried out in a non-protonic solvent, and the intermediate I is dissolved into the non-protonic solvent, wherein, an amount of the solvent is 30 times the mass of the intermediate I; then anhydrous sodium iodide is added, and heating reflux is carried out for 1 hour, wherein, a molar ratio of the intermediate I to anhydrous sodium iodide is 1:1.1; prior to the reaction, 2-amino phenyl mercaptan and alkali are dissolved into water at first, and then subjected to heating reflux for 2 hours together with a product obtained by activation, wherein, a molar ratio of the intermediate I to 2-amino phenyl mercaptan is 1:1.1, and a molar ratio of 2-amino phenyl mercaptan to alkali is 1:2; the alkali is sodium hydroxide, potassium hydroxide, cesium hydroxide, sodium carbonate, potassium carbonate or cesium carbonate; and the non-protonic solvent is N,N-dimethylformamide.

4. The method according to claim 1, wherein, the reaction in step (3) is carried out in a non-protonic solvent, substituted benzoic acid is added and then condensed for 1-36 hours with the intermediate II at 0-70° C. in the presence of the condensing agent while heating and stirring are carried out, and recrystallization or column chromatography purification is carried out; wherein, the non-protonic solvent is dichloromethane, ethyl acetate, N,N-dimethylformamide, N,N-dimethylacetamide or pyridine; the condensing agent is methyl chloroformate, ethyl chloroformate, ter-butyl chloroformate, carbonyl diimidazole (CDI), sulfonyl chloride, Boc anhydride, N,N-dicyclohexyl carbodiimide (DCC), 6-chlorobenzotriazole-1,1,3,3-tetramethylurea hexafluorophosphate, O-benzotriazole-N,N,N'N"-tetramethylurea tetrafluoroboric acid, 2-(7-oxidized benzotriazole)-N,N,N'N'-tetramethylurea hexafluorophosphate, 1-(3-dimethylaminopropyl)-3-ethylcarbodiimide, 1-hydroxylbenzotriazole, 1H-benzotriazole-1-oxotripyrrolidyl hexafluorophosphate, oxalyl chloride and thionyl chloride.

* * * * *